US00PP13353P3

(12) United States Plant Patent
Mukherjee et al.

(10) Patent No.: US PP13,353 P3
(45) Date of Patent: Dec. 10, 2002

(54) GLADIOLUS PLANT NAMED 'ANURAG'

(75) Inventors: Devashish Mukherjee, Palampur (IN); Devendra Dhayani, Palampur (IN); Jaichand Rana, Simla (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/817,137

(22) Filed: Mar. 27, 2001

(65) Prior Publication Data

US 2002/0144324 P1 Oct. 3, 2002

(51) Int. Cl.[7] ..... A01H 5/00

(52) U.S. Cl. ..... Plt./301

(58) Field of Search ..... Plt./301

*Primary Examiner*—Bruce R. Campell
*Assistant Examiner*—A Para
(74) *Attorney, Agent, or Firm*—Foley & Lardner

(57) ABSTRACT

A novel and distinct cultivar of Gladiolus plant named 'Anurag' particularly characterized by the combined features of light reddish purple (RHS-74D) flowers with dark reddish purple (RHS-66A) color blotches at both sides of the petals; at least 1.7 spikes per plant; 120 cm long flower spike; and approximately 16 flowers per spike.

1 Drawing Sheet

LATIN NAME OF THE GENUS AND SPECIES OF THE PLANT CLAIMED

*Gladiolus hybrid* sp.

VARIETY DENOMINATION

Anurag.

BACKGROUND OF THE INVENTION

The present invention relates to a new and distinct cultivar of Gladiolus known by the cultivar name 'Anurag'. The novel plant is a hybrid derived from the cross of *Gladiolus hybrid* 'Her Majesty' (unpatented) and *Gladiolus hybrid* 'Aldebaran' (unpatented). 'Anurag' was discovered and selected as one flowering plant within the progeny of the stated cross by or under the supervision of the inventors Devendra Dhayani, Devashish Mukherjee, and Jaichand Rana in a controlled environment in Palampur, Himachal Pradesh, India in 1991. 'Anurag' is propagated vegetatively by corms and hence can be maintained as a stable genotype.

The modern garden cultivars of Gladiolus come from diverse genetic parentages. Consequently, the genus is genetically complex. The available modern cultivars are so compelx genetically that the offspring obtained by crossing them segregate diverse selections that differ phenotypically [(Misra, 1975) Gladiolus Br. Assn. Newsletter, No.12, pp. 2–5].

The inventors initiated a breeding program to develop better types of Gladiolus hybrids suitable for a wide range of climatic conditions, and having wide range of characteristics such as better color, increased number of florets and spike length as per the international standards, better yield of corms and cormels, tolerant to the common diseases, among others. The collected germplasm of Gladiolus was planted for their propagation and multiplication. In this breeding program, the conventional hybridization breeding methods were used for breeding. More than 100 cross combinations were made by using distinct varieties such as 'Oscar', 'Jester', 'Snow Princess', 'Eurovision', 'Ballerina', 'King Liar', 'Cherry Blossom', 'Her Majesty', 'Green woodpecker', 'Friendship', 'Vink's' 'Glory', 'Aldebaran', 'Red Beauty', 'Top Brass', 'Copper King', 'Bonfire', 'White Goddess', 'Sunny Boy', 'Tropic Sea', and 'Friendship Pink' (unpatented varieties).

Many seedlings came out from a single cross combination. These plants were critically evaluated and tagged as per the desired color combinations, growth and flowering parameters. The corn and cormels of the selected hybrid plants were replanted continuously four years in the field for further evaluation and multiplications. Based on the superior performance for attractive color combination, compactness of flower spike, number of flowers per spike, length of flower spike, number of corm and cormels per plant evaluation and selection of superior quality hybrids were made.

The program yielded a number of hybrid plants out of which one genotype 'IHBT-GH-168' was selected and named 'Anurag'. This plant was found to have new color, flower size, number of florets per spikes, length of flower spikes, better yield of corm and cormels and less prone to common diseases.

BRIEF DESCRIPTION OF THE INVENTION

The following traits have been repeatedly observed and are determined to be basic characteristics of 'Anurag' which in combination distinguish this Gladiolus as a new and distinct cultivar:

1. Light reddish purple (RHS-74D) flowers with dark reddish purple (RHS-66A) color blotches at the edges of the petals;

2. Flowering period of approximately 92 days;

3. 1.7 flower spikes per plant on average;

4. Average length of flower spikes is 120 cm; and

5. Approximately 16 flowers per spikes.

'Anurag' has been developed through planned breeding experiments conducted in Palampur, Himachal Pradesh, India. Gladiolus varieties were collected from different sources and growth in the fields at Palampur, India for facilitating breeding program. The emasculation and pollination in different varieties were carried out in April–May, 1991. The seeds were collected in July–August, 1991 and sown in beds under open field conditions and covered with dry grasses in December, 1991. The resultant seedlings were space planted in the field at Palampur in March-April 1992. The corms and cormels of survived hybrid plants were replanted continuously four years for screening and multiplication.

Based on the superior performance and an attractive color combination, compactness of flower spikes, number of flowers per spikes, length of flower spikes, number of flowers remains open at a time, number of corm and cormel production per plant, the plant of this invention, 'Anurag' was selected for further observation and evaluation. 'Anurag' has compact flower spikes, numerous flowers, a ruffled ness of flower petals, and is not susceptible to common diseases. 'Anurag' is bi-colored, with flowers that are light reddish purple (RHS-74D) with dark reddish purple (RHS-66A) color blotches at the edges of the petals. In comparison to the parental cultivars, the primary difference is in color. 'Her Majesty' is sky blue and light blue in color, and 'Alderbaran' is straw-yellow with red blotches at the throat.

'Anurag' was grown at row distance of 1 foot and plant to plant distance of 6 inches for 4 consecutive years to study its growth and flowering performance and multiplication. Data were recorded on randomly selected twenty plants every year. 'Anurag' maintained uniformity in its growth and flowering performance. 'Anurag' has remained stable and uniform for its morphological characters and showed consistency in performance for various growth and flowering parameters during its evaluation and vegetative multiplication since 1992. Throughout the evaluation period of 'Anurag' no variants were found from the normal population.

BRIEF DESCRIPTION OF THE DRAWING

FIG. 1 is a photograph of a field grown flower spike of 'Anurag' depicting its light reddish purple (RHS-74D) flowers with dark reddish purple (RHS-66A) color blotches at the edges of the petals.

DETAILED DESCRIPTION OF THE INVENTION

In the following description color references are made to The Royal Horticultural Society Colour Chart. The color values were determined in Palampur, Himachal Pradesh, India. The age of the plant described is between 10 and 11 years old. 'Anurag' was grown under open field conditions in Palampur, Himachal Pradesh with an altitude of 1300 m above sea level, sub-humid climate, sub-temperate zone with an average maximum temperature of 30° C. and an average minimum temperature of 10° C., and average annual rainfall of approximately 250 cm.

Classification:

*Genus.*—Gladiolus.
*Species.*—Hybrid sp.
*Family.*—Iridacae.
*Common name.*—Sward lily/Gladiolus.

Plant:

*Plant height.*—134.52 cm.
*Growth habit.*—Erect, uniform.
*Stem diameter.*—1.03 cm.

Leaves:

*Number of leaves per plant.*—6.98.
*Height of leaves.*—61.81 cm.
*Size of leaves.*—Length 32.6–70.3 cm (52.87 average); width 2.3–4.5 cm (3.5 average).
*Shape.*—Linear lanceolate, flattened.
*Base.*—Cuneate.
*Apex.*—Acute/acuminate.
*Margin.*—Entire.
*Color.*—RHS 137 C (upper surface slightly darker than lower surface).
*Texture.*—Tough, glabrous upper and lower surfaces, scabrid due to strong venation.
*Veination.*—Parallel, multicostate, prominent, white and fibrous.

Flowers:

*First flowering.*—92 days.
*Flower color.*—Light reddish purple (RHS-74D) with dark reddish purple (RHS-66A) color blotches at both side of the petals edges.
*Petals* (*tepals*).—Type: Ruffled, perianth, petaloid. Number: 6 tepals on few whorls, stalked, 3 in each inner and outer whorls. Shape: Oblong oblanceolate to lanceolate, oblique. Width: 3–5.5 cm. Length: 5–8.5 cm. Margin: Entire. Texture: Smooth, glabrous.
*Buds.*—Length: 5.62–7.12 cm (6.10 average). Diameter: 1.08–1.58 cm (1.27 average). Color: RHS 51 C with blotches of RHS 66 A at the edges.
*Fragrance.*—None.
*Number of flowers remaining open at a time.*—7–8.
*Flower longevity.*—4–5 days.
*Flower diameter.*—11.3 cm.
*Spikes.*—Number of spikes per plant 1.70. Length of the flower spike: 120 cm. Number of flowers per spike: Approximately 16 . Spike Longevity: 10.2 days.
*Corms.*—Number of corms per plant: 1.55. Diameter of corms: 6.12 cm.
*Cormels.*—Number of cormels per plant 75.

Reproductive organs:

*Androecium.*—Stamen: 3, triandrous arranged in a whorl, adnate to perianth segments at the base. Filaments: 3–3.5 cm long, purple/pink to white in color. Anthers: 1.5–1.75 cm long, 2 lobed, purple/violet in color.
*Gynoecium.*—Ovary: Tricarpellary, inferior, many ovules in each locule. Style: Single, 6–6.5 cm long, terminal, white-green color. Stigma: Tri-lobed, pinkish-white color, 4 mm long, wavy margins, oblique.
*Seed/fruit.*—No known information.

I claim:

1. A novel and distinct cultivar of Gladiolus plant named 'Anurag' as described and illustrated herein.

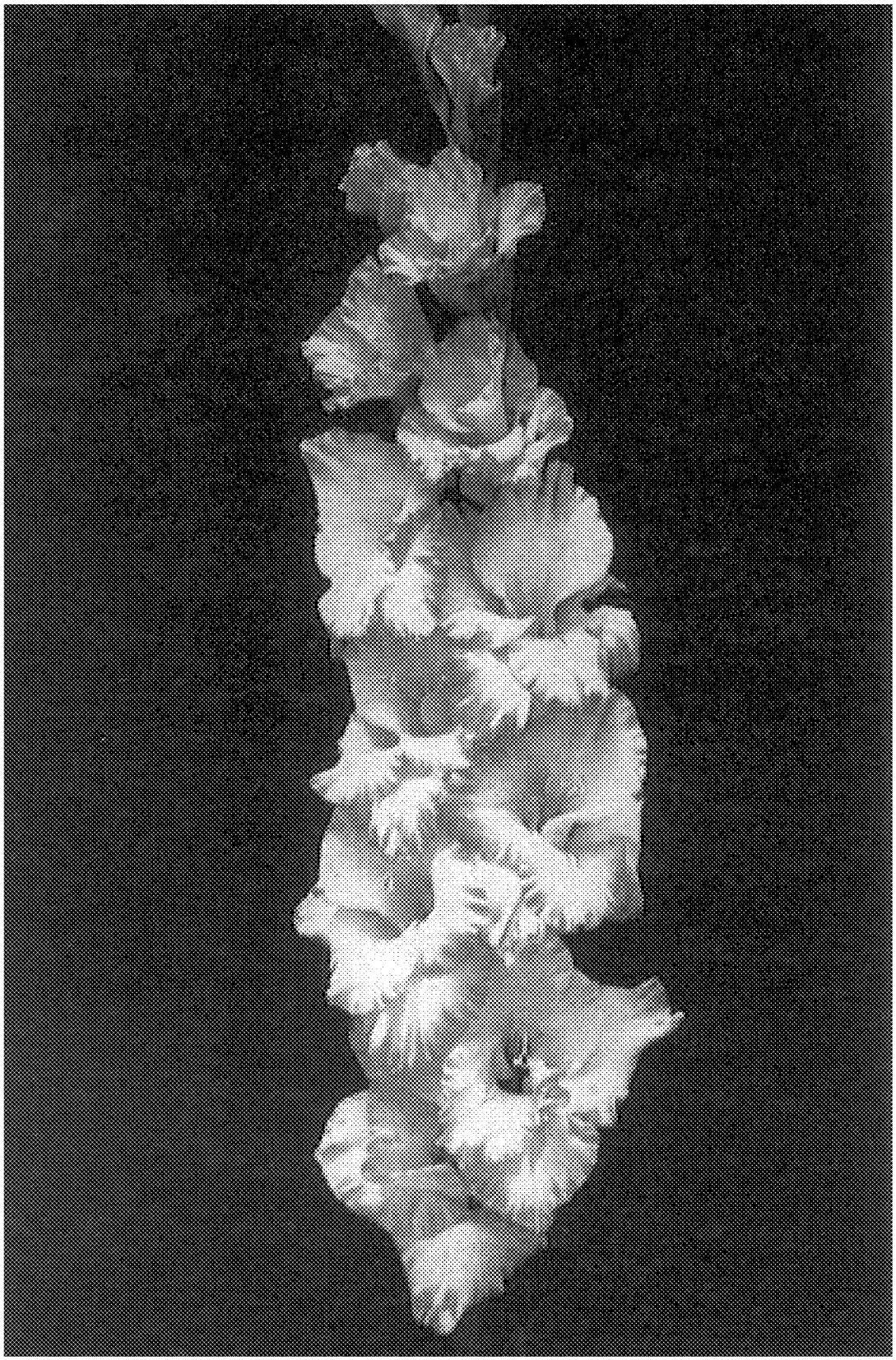

* * * * *